(12) United States Patent
Kan et al.

(10) Patent No.: US 7,588,778 B2
(45) Date of Patent: Sep. 15, 2009

(54) DELIVERY CARRIER FOR TARGETING TO CELLS EXPRESSED WITH SOMATOSTATIN RECEPTORS

(75) Inventors: Pei Kan, Hsinchu (TW); Ae-June Wang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 554 days.

(21) Appl. No.: 10/747,125

(22) Filed: Dec. 30, 2003

(65) Prior Publication Data

US 2004/0219205 A1    Nov. 4, 2004

(30) Foreign Application Priority Data

Dec. 31, 2002    (TW) .............................. 91138147 A

(51) Int. Cl.
*A61K 9/127*    (2006.01)
*A61K 31/355*    (2006.01)
*C07D 311/00*    (2006.01)

(52) U.S. Cl. ........................ 424/450; 514/458; 549/410

(58) Field of Classification Search ................. 424/450; 549/410; 514/458
See application file for complete search history.

(56) References Cited

U.S. PATENT DOCUMENTS

| 2002/0094964 A1 * | 7/2002 | Chen et al. ..................... 514/44 |
| 2003/0203038 A1 * | 10/2003 | Vail ............................. 424/490 |
| 2003/0229013 A1 * | 12/2003 | Wu et al. ....................... 514/7 |

\* cited by examiner

*Primary Examiner*—Michael G Hartley
*Assistant Examiner*—Leah Schlientz
(74) *Attorney, Agent, or Firm*—Bacon & Thomas, PLLC

(57) ABSTRACT

The present invention relates to a delivery carrier including liposomes or nanoparticles for targeting the cells expressed with somatostatin receptor, consisting of a plurality of liposomes that have one phospholipid bilayer coating, one hydrophilic core and a bioactive substance. The bioactive substance is packaged in the hydrophilic core, or embedded in the phospholipid bilayer, or electrically bound with liposomes as a complex, wherein the phospholipid bilayer coating is conjugated with a plurality of molecules in the outer surface. The molecules recognize the somatostatin receptor in the surface of the target cells and induce receptor-mediated endocytosis.

8 Claims, 3 Drawing Sheets

DELIVERY CARRIER FOR TARGETING TO CELLS EXPRESSED WITH SOMATOSTATIN RECEPTORS

BACKGROUND OF THE INVENTION

1. Field of the Invention

The present invention relates to a drug delivery carrier and, more particularly, to a drug delivery carrier of a nanoparticle used for transporting target molecules to the cells expressed with somatostatin receptors.

2. Description of Related Art

Somatostatin is an endogenous regulator related to the endocrine system, whose relative molecule, a somatostatin receptor, is usually distributed in the endocrine systems or digestive organs of the healthy body. Recently, some studies have indicated that the somatostatin receptor is also overexpressed in the tumor cells of some cancer patients. The somatostatin receptor is found in small cell lung cancer (SCLC), ovarian cancer, breast cancer, lymphoma, leukemia, astrocytoma, meningioma, renal cancer, cancers in gut, central neural and neuroendocrine systems and is also reported clinically in hepatic cellular carcinoma and carcinoid cancer. Several somatostatin analogues were developed and, in general, used for radioactive imaging in medical diagnosis to locate the tumor in the cancer patients, or treatment with radiotherapy, see U.S. Pat. Nos. 6,358,491, 6,241,965, 5,871, 711 and 5,814,298. Recently, a prodrug has been synthesized by chemically conjugating octreotide and related drugs for the target medication in a breast cancer cell (MCF-7), see U.S. Pat. No. 6,191,290. However, prodrug is rather smaller than liposomes or nanoparticle carriers which can provide enhanced accumulation in tumor site because of the designed particle size. In addition, lipsosomes or nanoparticle carriers also offer multi-ligands on the surface of the liposomes to bind with somatostatin receptors of the cells. The interaction will help liposomes or nanoparticle carriers to enter cell effectively. In another aspect, it is found that the somatostatin receptor is also expressed in the angiogenic vein vessels adjacent to some tumors. Researcher used somatostatin analogues to treat cancer by inhibition of angiogensis around tumors. Therefore, liposomes or other nanoparticles resulted from the conjugation of somatostatin (or somatostatin analogues) with lipids or (polymers) can target to the somatostatin receptor-expressed tumors or angiogenic vascular cells. Furthermore, due to the diversity and large capacity of liposomes and nanoparticles, they may carry genes or drugs and deliver them into specific cells through endocytosis for the desired therapy.

The particles used in the present administration system, such as liposomes or polymers, are in submicron level and cannot perform the selectivity or active targeting to specific cells. Therefore, it is required to develop a ligand for introducing nanoparticle administration system to selectively target the receptor-specific cells and thus improve the potency and further reduce side effects. At present, an antibody is used for this purpose, see U.S. Pat. Nos. 6,316,024, 6,300,319 and 6,004,534. However, the antibody is also involved in the immune response. That is, once the antibody is conjugated to the particle surface for the aforesaid purposes, an unpredictable immune response may occur inside the body. Another question is, due to the larger particle size of the aforesaid liposomes (or polymers) administration system, the particles introduced to the specific cell surface via the antibody may not enter the target cells via receptor-mediaetd endocytosis.

Therefore, to develop somatostatin (or somatostatin analogue) as a ligand for introducing an administration system of nanoparticles in targeting a specific tumor or angiogenic vessel surface, for inducing endocytosis of the aforesaid cells, and for enhancing the drug or gene delivery, has become the immediate challenge.

The new generation of active targeting administration system utilizes a ligand that can recognize the target cells to selectively introduce a drug to these specific target cells. For example, an antibody [U.S. Pat. Nos. 6,316,024, 6,300,319 and 6,004,534], an antibody fragment [U.S. Pat. Nos. 6,056, 973 and 6,043,094], a peptide [Cancer Res. 61:3978-85 (2001), BBA 1514(2):303-17 (2001) and J. Control Release 74:129-134 (2001)] or a small molecule compound is used as a ligand conjugated on the particle surface to assist liposomes to target the specific cells selectively. However, most of these ligands merely act on the specific cell surface and are not certain to induce the receptor-mediated endocytosis of the aforesaid specific cells, hence, the capacity for the system for delivering drugs into the cells may not reach the level anticipated and desired.

The somatostatin analogue can be regarded as a drug for gastrointestinal system cancer therapy, and moreover, it is also used for radioactive diagnosis and therapy. Most patent literatures related to somatostatin analogue focus on the treatment for gastrointestinal system cancer. Actually, many medical products of somatostatin analogue have already applied extensively in clinical therapy. In addition, a somatostatin analogue is chemically conjugated with paclitaxel to form a prodrug for the cancer target or for carrying a radionuclide for regional radiotherapy. However, the somatostatin analogue is yet to be taken as a ligand located on surface of liposomes or nanoparticles.

The vascular wall adjacent to the tumor is looser than the normal, so more nutrients are allowed to supplement. The vascular wall has a pore size around 200 nanometers (nm). Therefore, in the current study, for improving the circulating time in blood and for achieving the accumulation of the particles in the tumor, the liposome size is controlled in an order of around 100 nm and the hydrophobility of the liposome surface is modified. However, in this situation, the range of the liposome size is largely restricted. The alternative is to change the target (e.g. vascular cells adjacent to tumors instead of vascular wall) of drug delivery in tumor treatment. If the vascular cells adjacent to the tumor is taken as an object for target therapy, the particle size range can be enlarged the threshold size of actual endocytosis.

SUMMARY OF THE INVENTION

The object of the present invention is to provide a delivery carrier for targeting the cells expressed with a somatostatin receptor, and for transporting the enveloped drug to the cells expressed with somatostatin receptors.

To achieve the object, the present invention provides a delivery carrier for targeting the cells expressed with a somatostatin receptor, includes a plurality of liposomes of phospholipid bilayers, and at least one bioactive substance; wherein the outward surface of the phospholipid bilayer is conjugated with a plurality of molecules, and the molecules comprise at least one ligand that recognizes the somatostatin receptor and induces receptor-mediated endocytosis. By conjugated with a plurality of molecules it is understood, in the present application that, one end of the spacer residue is conjugated with a lipid, and therefore inserted into the liposome of the phospholipid bilayers.

It is known that the somatostatin receptor targeted by somatostatin analogues is mainly distributed in the endocrine and gastrointestinal systems. However, it is found that several tumors also have over-expressed patterns. Therefore, the somatostatin receptors are always taken as the object for targeting. In some cases, somatostatin receptors are over-expressed in the vascular wall adjacent to several tumors, which even did not express excessive somatostatin receptors. Hence, nanoparticles conjugated with a somatoatatin analogue may not only carry cytotoxic drugs to the tumor cells for target therapy, but also carry the anti-angiogenic substances for targeting the vessels adjacent to the tumor. By delivery of the anti-angiogenic substances to the vascular cells peripheral to tumors, it can indirectly suppress the proliferation and migration of the tumors. Moreover, the complex of the nanoparticles conjugated with a somatoatatin analogue can carry genetic substances or proteins for targeting the vascular cells adjacent to the tumor for the gene therapy or immune therapy.

In the present invention, the usage of the somatostatin analogue as a ligand will not only target the specific cell surface, but also accelerate the endocytosis of nanoparticles into the cells by somatostatin receptor-mediated endocytosis process thereof. Other reports have proved that endocytosis is triggered by the binding of the somatostatin analogue and the somatostatin receptor on the cell surface.

In the present invention, the surface side of a nanoparticle is conjugated with a somatostatin analogue to serve as a delivery carrier. Due to the diversity and large capacity of the nanoparticles, the particles alter the pharmacokinetics and distribution properties of the drugs. In addition, the amounts of drugs carried by each somatostatin analogue unit increase according to the assistance of the diversity and large capacity of the nanoparticles. Moreover, various types of bioactive substances such as chemical compounds, proteins, peptides, DNA, phase contrast agent, therapeutic reagents and diagnostic reagents can be carried by the nanoparticles of the present invention. These agents carried by the nanoparticles can be introduced into the specific cells selectively and specifically for target delivery purposes.

Other objects, advantages, and novel features of the invention will become more apparent from the following detailed description when taken in conjunction with the accompanying drawings.

DETAILED DESCRIPTION OF THE PREFERRED EMBODIMENT

For the understanding of the present art by the those skilled in the art, there are eleven preferred embodiments specifically described as follows.

Embodiment 1

Synthesis of the Octreotide-TPGS

Figure 1:
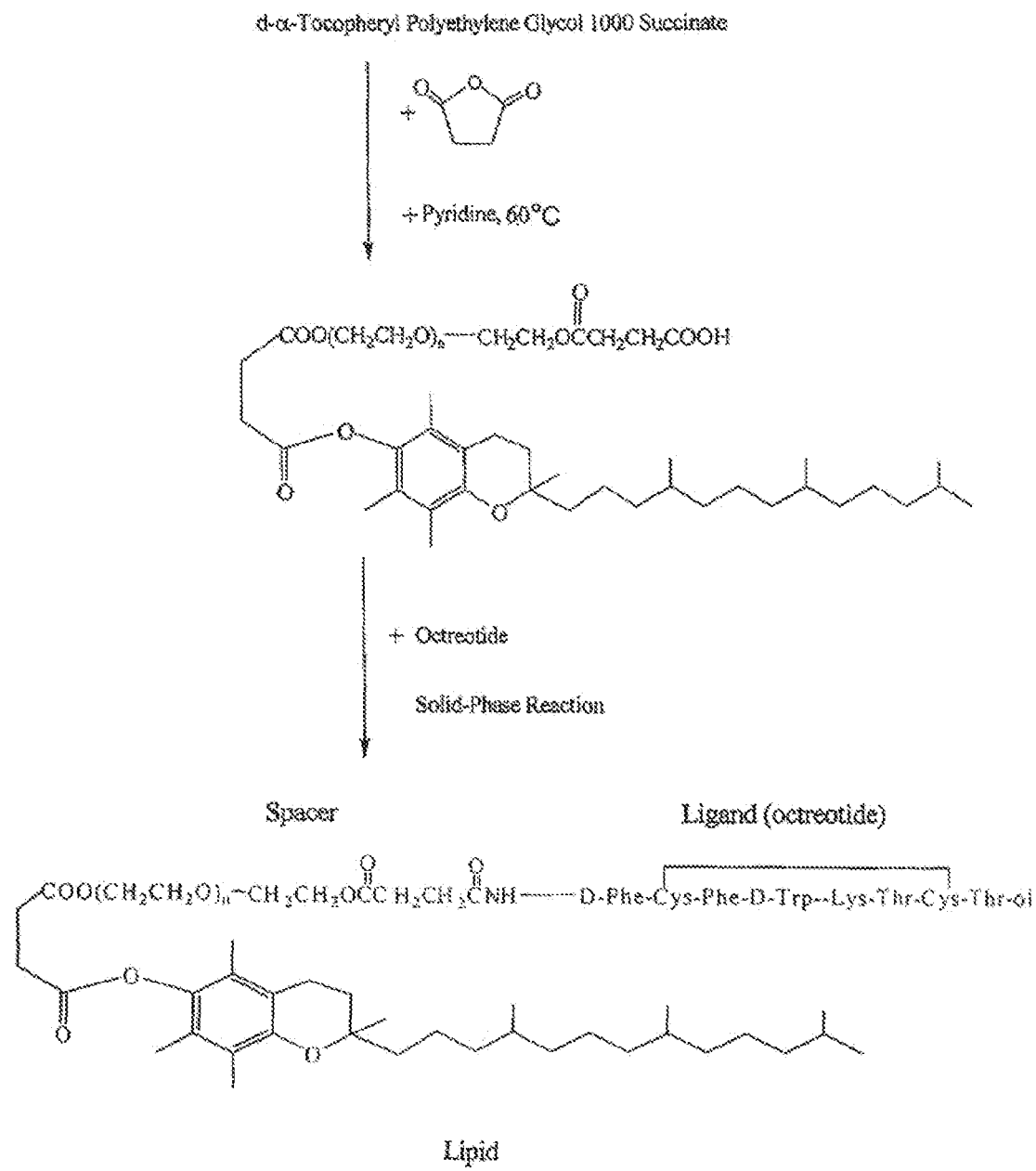
FIG. 1 is the synthetic process of Octreotide-TPGS of the present invention.

Octreotide is one of the somatostatin analogues synthesized by the modified procedure of the solid phase peptide synthesis, and a known drug for clinical use. The scheme of synthesis is shown as FIG. 1. First, p-carboxybenzaldehyde is used as a conjugating reagent for fixing Fmoc-threoninol octreotide on the amine-resins (0.1 mmole) to form octreotide with C-terminal alcohol. Then d-α-tocopheryl polyethylene glycol 1000 succinate (TPGS) (0.1 mmole) and succinic anhydride (0.1 mmole) are dissolved in 5 ml of pyridine and stirred for 3 hr at room temperature. TPGS succinate is extracted via crystallization in the final step of the reaction. The TPGS succinate is then activated by PyBOP in the DMF and conjugated to the amino terminal of the NH$_2$-D-Phe-c [Cys-Phe-D-Trp-Lys(Boc)-Thr-Cys]-Thr-ol-acetal amide resin. Under the condition of 1% TFA/5% TIS/dichloromethane (DCM), the peptide conjugate is cleaved from the amino resin, and the side chain is then de-protected. The product is further adjusted to be neutral by 15% pyridine/methanol to obtain a final product as formula (I).

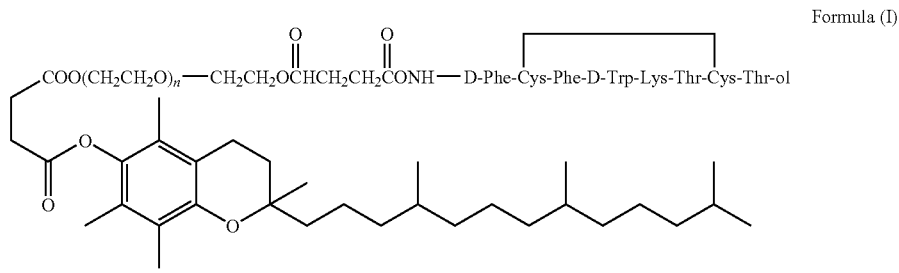

Formula (I)

wherein, n means an integral between 10 to 30.

The sample is further lyophilized and stored in a nitrogen gas refrigerator.

Embodiment 2

Synthesis of the Octreotide-PEG$_{1500}$-Cholesterol

Octreotide is one of the somatostatin analogues synthesized by the modified procedure of the solid phase peptide synthesis, and a known drug for clinical use. The synthesis process is shown as FIG. 1. First, p-carboxybenzaldehyde is used as a conjugating material for fixing Fmoc-threoninol octreotide on the amine-resins (0.1 mmole) to form octreotide with C-terminal alcohol. Then $PEG_{1500}$-Cholesterol (0.1 mmole) and succinic anhydride (0.1 mmole) are dissolved in 5 ml of pyridine and stirred for 3 hr at room temperature. $PEG_{1500}$-Cholesterol succinate is extracted via crystallization in the final step of the reaction. $PEG_{1500}$-Cholesterol succinate is then activated by PyBOP in the DMF and conjugated to the amino terminal of the $NH_2$-D-Phe-c[Cys-Phe-D-Trp-Lys(Boc)-Thr-Cys]-Thr-ol-acetal amide resin. Under the condition of 1% TFA/5% TIS/dichloromethane (DCM), the peptide conjugate is cleaved from the amino resin, and the side chain is then de-protected. The product is further adjusted to be neutral by 15% pyridine/methanol to obtain a final product as formula (II).

Formula (II)

wherein, m means an integral between 20 to 40.

The sample is further lyophilized and stored in a nitrogen gas refrigerator.

Embodiment 3

Synthesis of the Octreotide-$PEG_{3400}$-DSPE

Figure 2:
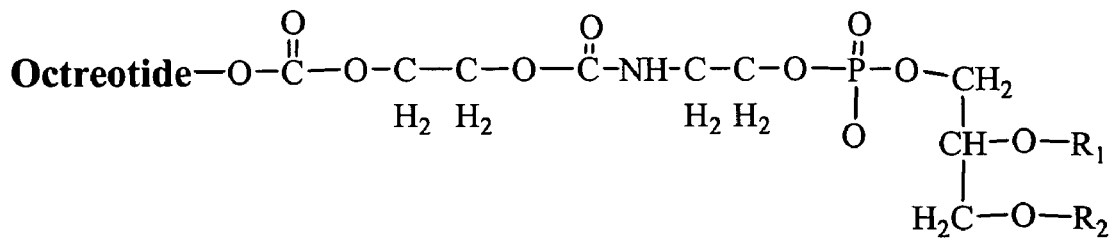
FIG. 2 is the structure of Octreotide-PEG$_{3400}$-DSPE of the present invention.

First, p-carboxybenzaldehyde is used as a conjugating material for fixing Fmoc-threoninol octreotide on the amine-resins (0.1 mmole) to form octreotide with C-terminal alcohol. NHS-$PEG_{3400}$-DSPE is activated by PyBOP in the DMF and conjugated to the amino terminal of the NH2-D-Phe-c [Cys-Phe-D-Trp-Lys(Boc)-Thr-Cys]-Thr-ol-acetal amide resin. Under the condition of 1% TFA/5% TIS/dichloromethane (DCM), the peptide conjugate is cleaved from the amino resin and the side chain is then de-protected. The product is further adjusted to be neutral by 15% pyridine/methanol, and the sample is further lyophilized and stored in a nitrogen gas refrigerator. The product of the present embodiment is shown in FIG. 2.

Embodiment 4

Preparation of the CF-Liposomes

Liposomes are prepared by a conventional thin film process. A mixture of about 20 mg of lipid and Octreotide-TPGS with a specific ratio based on the formulations in Table 1 is dissolved in 20 ml of methanol, and the thin film process is processed under nitrogen gas condition. Then 200 mM of fluorescent substance (CF, carboxy fluoresceine) is added in the mixture when hydration is carried out, and the CF is entrapped in the liposomes. Additionally, 1 ml of CF solution (40 mM CF, 300 Osm) is added and shaken for 40 min under 18° C. for further hydration process. Then ultra-sonicator is used to minimize the particle size, and the Sephadex G75 column (18 cm×1.5 cm) is further used to separate the liposomes and un-entrapped free CF, wherein the eluent is Tris-Buffer (pH=7.4, 290 Osm). The concentration of CF incorporated in the liposome hydrophilic core is monitored at excitation wavelength of 470 nm and emission wavelength 520 nm. No detectable leakage of CF from the liposomes ocurred in 4 hrs of monitoring period. The CF-liposome size is determined by the Laser-Doppler Particle Analyzer. The CF-liposome formulations and various properties are shown as Table 1.

TABLE 1

Properties of the Liposome in the Embodiment 4

| Formulation | Mean Particle Size | CF Conc. |
|---|---|---|
| HEPC/Chol/Oct-TPGS (3/1/0.015) | 488.0 ± 277.9 nm | 124 mM |
| HEPC/EPC/Chol/TPGS/Oct-TPGS (1.5/1.5/1/0.075/0.015) | 114.9 ± 40.4 nm | 200 mM |
| HEPC/EPC/Chol/Oct-TPGS | 130.0 ± 60.2 nm | 61.8 mM |

TABLE 1-continued

Properties of the Liposome in the Embodiment 4

| Formulation | Mean Particle Size | CF Conc. |
|---|---|---|
| (1.5/1.5/1/0.015) | | |
| HEPC/EPC/Chol/Oct-TPGS (1.5/1.5/1/0.06) | 112.5 ± 48.9 nm | 249.7 mM |
| HEPC/Chol/TPGS (3/1/0.015) | 247.9 ± 101.9 nm | 110 mM |
| HEPC/EPC/Chol/TPGS (1.5/1.5/1/0.09) | 108.1 ± 43.1 nm | 190 mM |
| HEPC/EPC/Chol/TPGS (1.5/1.5/1/0.015) | 126.1 ± 53.1 nm | 238 mM |
| HEPC/EPC/Chol/TPGS (1.5/1.5/1/0.06) | 112.1 ± 45.4 nm | 321.2 mM |

Embodiment 5

Preparation of the DiI-Liposomes

Liposomes are prepared by a conventional thin film process. A mixture of about 20 mg of lipid and Octreotide-PEG-DSPE with a specific ratio based on the formulations in Table 2 is dissolved in 2 ml of organic solvent, and the thin film skill is processed under a nitrogen gas condition. Then the mixture is hydrated via a hydration solution (1 ML, 8% sucrose, 30 mM Tris, pH=7.5) for 10 min under 50° C., and the fluorescent probe—DiI is embedded in the hydrophobic domain of liposomal phospholipid bilayer at this time. Then the ultra-sonicator is used to minimize the particle size, and the size of the liposomes is determined by the Laser-Doppler Particle Analyzer. The liposome formulations and various properties are shown as Table 2.

TABLE 2

Properties of the Liposome in the Embodiment 5

| Formulation | Mean Partical Size | DiI Conc. |
|---|---|---|
| HSPC/Chol/MPEG (15/10/2) | 149.3 ± 58.8 nm | 10 mM |
| HSPC/Chol/MPEG/Oct-PEG-DSPE (15/10/1.5/0.5) | 146.6 ± 57.1 nm | 10 mM |

TABLE 2-continued

Properties of the Liposome in the Embodiment 5

| Formulation | Mean Partical Size | DiI Conc. |
|---|---|---|
| HSPC/Chol/MPEG/Oct-PEG-DSPE (15/10/1.75/0.25) | 126.7 ± 45.7 nm | 10 mM |
| HSPC/Chol/MPEG/Oct-PEG-DSPE (15/10/1.875/0.125) | 125.0 ± 44.3 nm | 10 mM |
| HSPC/Chol/MPEG/Oct-PEG-DSPE (15/10/1.95/0.05) | 105.7 ± 40.0 nm | 10 mM |

Embodiment 6

Preparation of the DNA-Liposome Complex

Liposomes are prepared by a conventional thin film process. A mixture of about 20 mg of lipid and Octreotide-PEG-DSPE with a specific ratio is dissolved in organic solvent, and the thin film skill is processed under a nitrogen gas condition with a final formulation of DSPG/DOPE/Octreotide-PEG-DSPE=49/49/2 (molar ratio). Equal volumes of the following solutions: FITC labeled oligonucleotide (F-ODN), calf thymus DNA mixed solution (0.1 mg/ml), 1.1 mg/ml of protamine solution, and 0.3 mg/ml of liposomes suspended solution are mixed to form the DNA-liposome complex. DNA is electrically bound with the liposomes to form a complex. The complex is then stood for 10 min at room temperature for further use. The particle size of the complex is about 150 to 200 nm, and the incorporation efficiency for the oligonucleotide (F-ODN) is 100%.

Embodiment 7

Endocytosis of the Liposomes by Different Cells

MCF-7 cells (somatostatin receptor-expressed) and CHO-K1 cells (without somatostatin receptor expression) are transferred into the six-well culture plates at 24 hrs before experiment, and each well contains $2\times10^5$ cells. To determine if the fluorescence-liposomes are taken up via receptor-mediated endocytosis, the MCF-7 and CHO-K1 cells are incubated with the liposomes with/without octreotide ligand, respectively. The two liposomes are diluted with a culture medium, and then 1 ml of 30 μM CF-liposome solution is added per well. After reaction for 0.5 hr at 37° C., each well is washed four times with PBS to remove the suspended liposomes. The cells are then fixed at 4° C. with 8% paraformaldehyde solution for 30 min. Finally, the cells are washed several times with PBS, and their fluorescence patterns are further observed with Nikon fluorescence microscope. The result shows that the endocytosis by different cells are not apparent for the liposomes with 0.5 mole % octreotide (OL312). However, once the octreotide content increases to 2 mol % (OL313), the octreotide-liposomes are taken up apparently by MCF-7 after co-incubated for 30 min. But the control liposomes without octreotide ligand fail to be taken up. In contrast, both the liposomes conjugated with/without octreotide ligand fail to be apparently taken up by CHO-K1 cells. The data show the selectivity of octreotide ligand in different cells. The above results show that octreotide can guide liposome, and can be selectively taken up by the tumor cells expressed with a somatostatin receptor, and therefore octreotide can be referred to as a suitable ligand for targeting. The content of octreotide conjugated to the liposome surface is at least 2 mole %, and by the shortly co-incubating for 30 min, the particles begin to apparently reinforce targeting thereof.

Embodiment 8

Effect of Different Size of Liposomes on Endocytosis of Tumor Cells

MCF-7 cell (somatostatin receptor-expressed) and CHO-K1 cell (without somatostatin receptor expression) are seeded on a six-well culture plate separately at 24 hrs before experiment, and each well contains $2\times10^5$ cells. Different sizes of Octreotide-liposomes are used after dilution with a culture medium, and 1 ml of 30 μM CF-liposome solution is then added per well. After reacting for 2 hr at 37° C., each well is washed four times with PBS to remove the suspended liposomes. Then the cells are fixed at 4° C. with 8% paraformaldehyde solution for 30 min. Finally, the cells are washed several times with PBS, and their fluorescence patterns are observed with a Nikon fluorescence microscope. The result shows that the liposomes with mean particle of 488 nm fails to be taken up by MCF-7. However, in comparison with other experiments with equal liposome formulation but smaller size, the fluorescent intensities are low but still detectable. It is indicated that when the mean particle size is 250 nm, the liposomes without octreotide ligand are also taken up a few when incubated with cells for 2 hrs. Therefore, it is concluded that a particle with the size more than 400 nm fails to be taken up by cells with the assistance of somatostatin receptor modulation.

Embodiment 9

Figure 3:
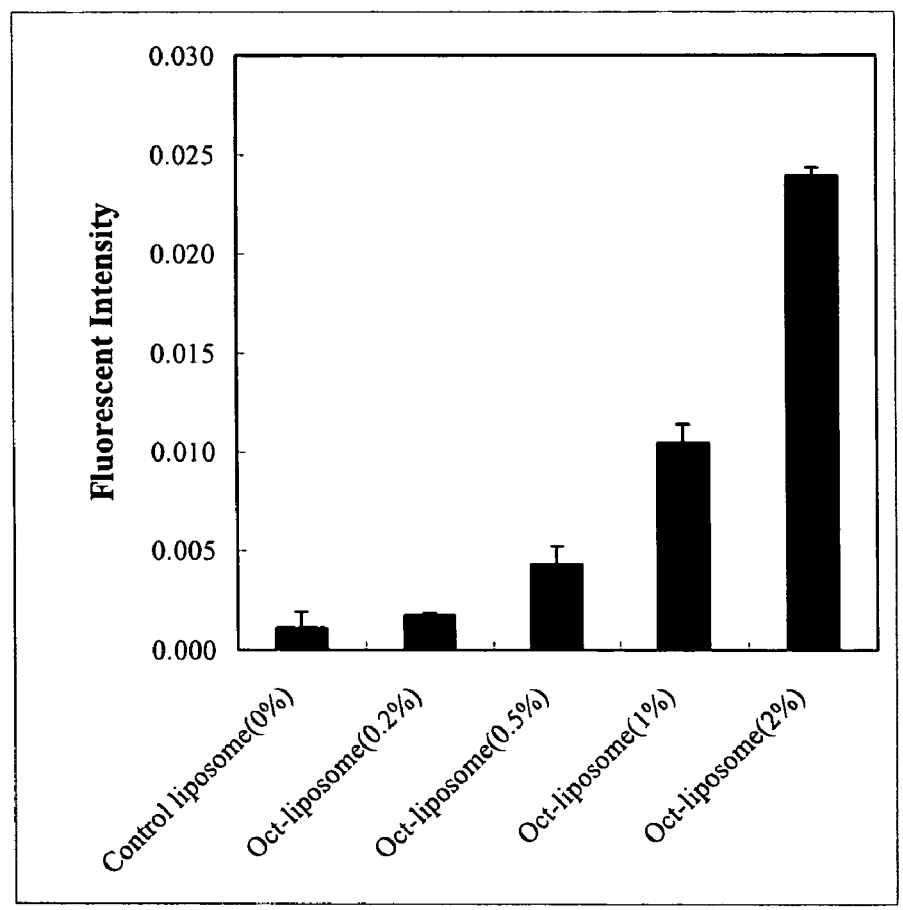
FIG. 3 shows the results of the liposomes with different surface somatostatin contents taken up by the MCF-7 of the present invention.

Effect of Different Octreotide Content of Liposomes on Endocytosis of Tumor Cells MCF-7 cells are seeded on a 24-well culture plate at 24 hrs before experiment, and each well contains of $5\times10^4$ cells. Different ratios of octreotide-PEG-DSPE to liposomes are used in the experiment. The liposomes are first diluted with the culture medium, and then the liposomes at 125 nmole lipid concentration are added to each well. After prolonging the reaction time to 4 hrs at 37° C., each well is washed four times with PBS to remove the suspended liposomes. Then the cells are lyzed by Triton X-100 solution and the DiI intensity quantitatively analyzed for endocytosis by a fluorescence photometer. The result is shown as FIG. 3. When the octreotide ligand content is 0.5 mol %, fluorescent intensity in the cells increases significantly ($p<0.05$) as compared to the control liposomes without octreotide ligands. The uptake of DiI-liposomes by cells further increases along with the octreotide contents. Therefore, once the octreotide content increases to 2 mol %, the efficacy of endocytosis increases by 20 folds. Due to the even distribution of octreotide ligands in both sides of the liposome bilayer, the endocytosis will increase effectively by a 4-hr reaction time only if the outside layer ligands are more than 0.25 mol %.

Embodiment 10

Endocytosis of Liposome by Human Umbilical Vein Cells

Figure 4:
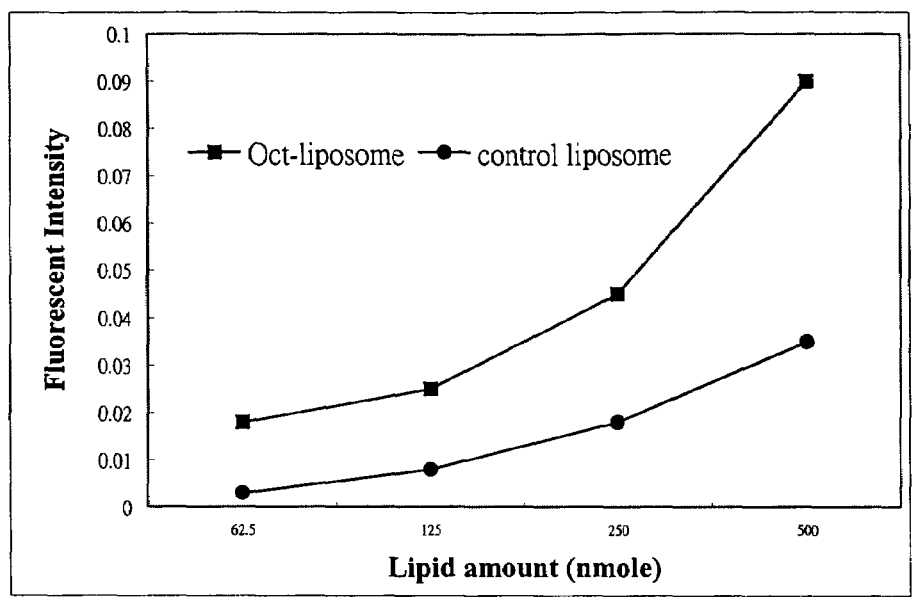
FIG. 4 shows the results of the liposomes with different lipid concentrations taken up by the HUVEC of the present invention.

The collagenase perfusion method is used to perfuse human umbilical cord. After collecting the human umbilical vein cells (HUVEC) for the primary culture, the cells are transferred into a six-well culture plate at 24 hrs before experiment, and each well contains of $2\times10^4$ cells. With use of 2 mole % octreotide-PEG-DSPE of liposomes for the experiment, the liposomes are first diluted with a serum-free culture medium, and then the liposomes of various lipid concentrations (62.6, 125, 250 and 500 nmole) are added to the HUVEC primary culture. After reacting for 4 hr at 37° C., each well is washed four times with PBS to remove the suspended liposomes. Then the cells are lyzed by Triton X-100 solution, and the DiI intensity for endocytosis are quantitatively analyzed by a fluorescence photometer. The result is shown as FIG. 4, wherein the endocytosis pattern increases significantly by 2 to 3-fold at this octreotide content.

Embodiment 11

Figure 5:
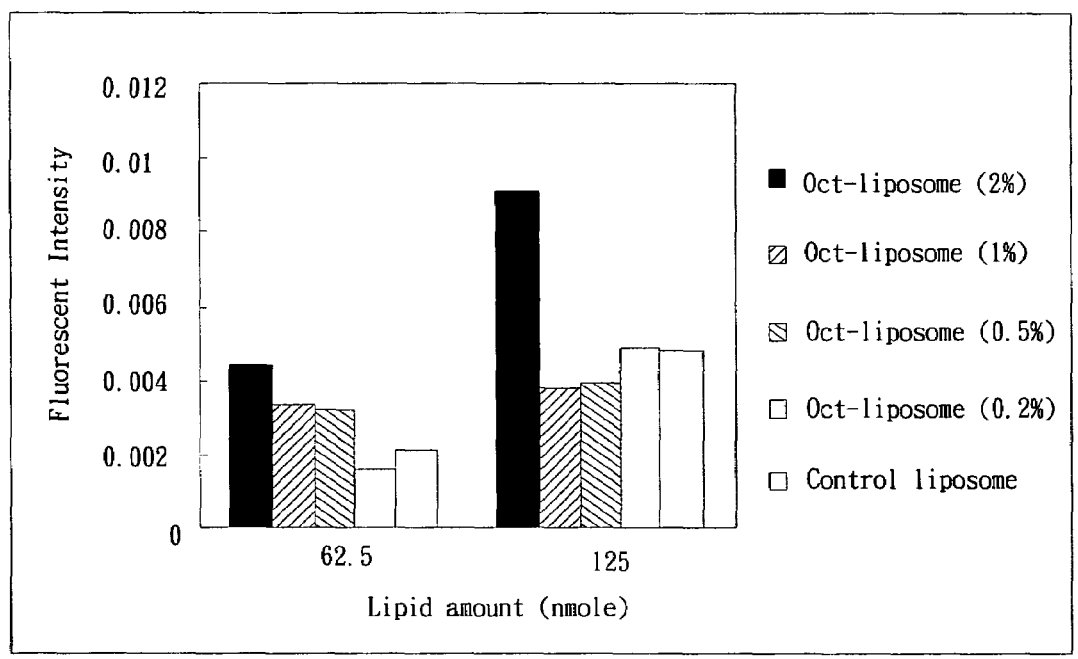
FIG. 5 shows the results of the liposomes with different surface octreotide contents taken up by the HUVEC of the present invention.

Effect of Different Octreotide Content of Liposomes on Endocytosis by HUVEC Cells HUVECs are seeded on a 24-well culture plate at 24 hrs before experiment, each well containing $2 \times 10^4$ cells. Different ratios of octreotide-PEG-DSPE to liposomes are used for the experiment. The liposomes are first diluted with a culture medium, and then the liposomes of two lipid concentrations (62.6 and 125 nmole) are added and compared. After reacting for 4 hr at 37° C., each well is washed four times with PBS to remove the suspended liposomes. Then the cells are lyzed by Triton X-100 solution, and the DiI intensity for endocytosis is quantitatively analyzed by a fluorescence photometer. The result is shown as FIG. 5, wherein the DiI intensity endocytosed by HUVECs increase significantly only if the octreotide content formulates at least 2 mol %. The efficacy of endocytosis rises to around 170%. Due to the diverse densities and bioactivities of the somatostatin receptors expressed by the distinct cell types, the somatostatin analogue content required for the liposome targeting will also change, and obviously more somatostatin contents of liposomes are required for the HUVEC targeting.

It is to be noted that the somatostatin analogue ligand which is conjugated to the liposome surface in the present invention can be modified according to the distinct receptors on the cell surface. The ligand of the present invention is preferably selected from the group consisting of somatostatin, somatostatin analogues and artificial somatostatin derivatives, more preferably selected from octreotide. Preferably, the liposome size used in the present invention is taken up via cell endocytosis, and the preferred particle size for the liposome is smaller than 400 nm. In the present invention, the ligand used on the liposome surface, whose formulation ratio in the liposome is unlimited, is preferably larger than 0.25% molar ratio in the liposome formulation. The ligand used in the present invention will conjugate directly to the liposome surface, or will further have a spacer residue between the ligand and the outward surface to enhance the opportunities of ligands on the liposomes for reaching the somatostatin receptors. The liposomes used in the present invention comprise at least one bioactive substance, and the bioactive substance is unlimited, preferably being selected from the group consisting of chemical compounds, peptides, proteins, DNA and a developing agent.

Although the present invention has been explained in relation to its preferred embodiment, it is to be understood that many other possible modifications and variations can be made without departing from the spirit and scope of the invention as hereinafter claimed.

What is claimed is:

1. A delivery carrier for targeting to cells expressed with a somatostatin receptor, comprising:
    a plurality of liposomes of phospholipid bilayers, and
    at least one bioactive substance;
    wherein the outward surface of said phospholipid bilayer has inserted therein a plurality of molecules, said molecules comprise at least one ligand that recognizes said somatostatin receptor and induces receptor-mediated endocytosis; and the molecule is ocetreotide-TPGS of formula (I):

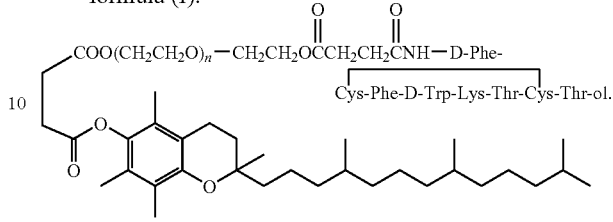

and n is an integer between 10 to 30.

2. The delivery carrier as claimed in claim 1, wherein each of said plurality of liposomes has a particle size that is smaller than 400 nanometers.

3. The delivery carrier as claimed in claim 1, wherein the molar ratio of said ligand to said liposome is larger than 0.25%.

4. The delivery carrier as claimed in claim 1, wherein said bioactive substance is selected from the group consisting of chemical compounds, peptides, proteins, DNAs and developing agents.

5. A compound of formula (I):

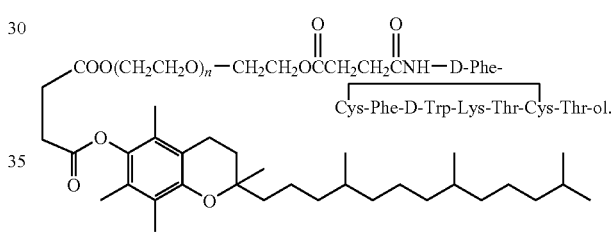

wherein n is an integer between 10 to 30.

6. The delivery carrier as claimed in claim 1, wherein each of said plurality of liposomes has a particle size that is smaller than 400 nanometers, the molar ratio of said ligand to said liposome is larger than 0.25%, and said bioactive substance is selected from the group consisting of chemical compounds, peptides, proteins, DNAs and developing agents.

7. A delivery carrier for targeting cells expressing a somatostatin receptor, comprising:
    at least one bioactive substance selected from the group consisting of chemical compounds, peptides, proteins, DNAs and developing agents; and
    a phospholipid bilayer comprising liposomes and molecules inserted on the outward surface of said phospholipid bilayer, wherein the molecules comprise at least one ligand that recognizes said somatostatin receptor, induces receptor-mediated endocytosis and has a structure of formula (I):

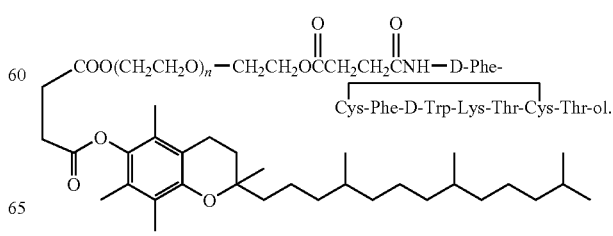

and n is an integer between 10 to 30.

8. The delivery carrier as claimed in claim 7, wherein said compound is a cytotoxic compound or anti-angiogenesis compound.

\* \* \* \* \*

UNITED STATES PATENT AND TRADEMARK OFFICE
CERTIFICATE OF CORRECTION

PATENT NO. : 7,588,778 B2  Page 1 of 1
APPLICATION NO. : 10/747125
DATED : September 15, 2009
INVENTOR(S) : Kan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1007 days.

Signed and Sealed this

Twenty-first Day of September, 2010

David J. Kappos
*Director of the United States Patent and Trademark Office*